United States Patent
Alshatwi et al.

(10) Patent No.: US 12,347,871 B1
(45) Date of Patent: Jul. 1, 2025

(54) SYNTHESIS OF POLYPEPTIDE CONJUGATED CARBON QUANTUM DOTS/METAL HYBRID NANOARCHITECTURES FOR BIOELECTRICITY HARVESTING IN MICROBIAL FUEL CELL

(71) Applicant: KING SAUD UNIVERSITY, Riyadh (SA)

(72) Inventors: Ali Abdullah Alshatwi, Riyadh (SA); Jegan A Athianrayanan, Riyadh (SA); Vaiyapuri Subbarayan Periasamy, Riyadh (SA); Taghreed Naser Almanaa, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/987,824

(22) Filed: Dec. 19, 2024

(51) Int. Cl.
| | |
|---|---|
| *H01M 4/90* | (2006.01) |
| *B82Y 40/00* | (2011.01) |
| *C07K 1/107* | (2006.01) |
| *C07K 14/47* | (2006.01) |
| *G01R 19/00* | (2006.01) |
| *H01M 8/04537* | (2016.01) |
| *H01M 8/16* | (2006.01) |

(52) U.S. Cl.
CPC ........... *H01M 4/9008* (2013.01); *B82Y 40/00* (2013.01); *C07K 1/1077* (2013.01); *C07K 14/47* (2013.01); *G01R 19/0084* (2013.01); *H01M 8/04552* (2013.01); *H01M 8/16* (2013.01)

(58) Field of Classification Search
CPC ... H01M 4/9008; C07K 1/1077; C07K 14/47; B82Y 40/00
USPC ....................................... 252/519.3
See application file for complete search history.

(56) References Cited

FOREIGN PATENT DOCUMENTS

| CN | 109239170 A | * | 1/2019 | ....... G01N 27/44747 |
| CN | 111437883 A | * | 7/2020 | .......... B01J 27/1853 |

OTHER PUBLICATIONS

Translation of CN109239170A (Year: 2025).*
Cui "Carbon Dots: Synthesis, Properties and Applications." Nanomaterials 2021, 11, 3419 (Year: 2021).*
Translation of CN111437883 (Year: 2025).*
Hasan, et al., "Formation of Carbon Quantum Dots via Hydrothermal Carbonization: Investigate the Effect of Precursors", Energies 2021, 14, 986, pp. 1-10, First available online Feb. 13, 2021.
Zhang, et al., "In vivo characterization of hair and skin derived carbon quantum dots with high quantum yield as longterm bioprobes in zebrafish", Sci Rep. 6:37860, pp. 1-12, First available online Nov. 25, 2016.
Guo, et al., "Thermal treatment of hair for the synthesis of sustainable carbon quantum dots and the applications for sensing Hg2+", Sci Rep. 6:35795, pp. 1-7, First available online Oct. 20, 2016.

* cited by examiner

*Primary Examiner* — Tri V Nguyen
(74) *Attorney, Agent, or Firm* — Nath, Goldberg & Meyer; Joshua B. Goldberg

(57) ABSTRACT

A method of making camel hair derived-polypeptide conjugated carbon quantum dots (CH-CQDs)-metal hybrid nanoarchitectures can include preparing a plurality of mixtures of water and camel hair derived-polypeptide conjugated carbon quantum dots (CH-CQDs) to obtain a plurality of camel hair derived-polypeptide conjugated carbon quantum dots (CH-CQDs) solutions; preparing a plurality of metal precursor solutions; individually adding one of each of the plurality of metal precursor solutions to one of each of the plurality of camel hair derived-polypeptide conjugated carbon quantum dots (CH-CQDs) solutions to obtain a plurality of resultant mixtures; and individually mixing each of the plurality of resultant mixtures to obtain a plurality of camel hair derived-polypeptide conjugated carbon quantum dots (CH-CQDs)-metal hybrid nanoarchitectures.

11 Claims, 12 Drawing Sheets

SYNTHESIS OF POLYPEPTIDE CONJUGATED CARBON QUANTUM DOTS/METAL HYBRID NANOARCHITECTURES FOR BIOELECTRICITY HARVESTING IN MICROBIAL FUEL CELL

FIELD AND BACKGROUND

The disclosure of the present application relates to a system, and particularly to a system and method of making camel hair derived-polypeptide conjugated carbon quantum dots (CH-CQDs)-metal hybrid nanoarchitectures and determining bioelectricity generation therefrom.

DESCRIPTION OF RELATED ART

Nanoscience and nanotechnology have remarkably improved and revolutionized many technology and industry sectors over the years. At present, a number of catalyst supportive materials have been fabricated, including $Al_2O_3$, silica, metal oxides, MXene, and carbon-based materials. Among these supportive materials, the carbon-based materials including carbon nanotubes, graphene, fullerenes, nanodiamonds, graphitic carbon nitrides, and carbon quantum dots have an engrossed growing attention for diverse electrochemical reaction applications. The high interest in carbon based-based materials is due to their intrinsic physical and chemical properties, such as outstanding mechanical strength, thermal and electrical conductivity, tunable porosity, and large surface area.

Due to global climate change and fossil fuel depletion, researchers are developing sustainable, renewable, and environmentally benign technologies for minimizing environmental pollutions as well as for providing alternative means of energy generation. One such technology is the microbial fuel cell (MFC), which offers the generation of renewable energy from waste substances using microorganisms. Also, MFC is a promising alternate energy generation technology that converts chemical energy into electrical energy using microorganisms. However, the currently available catalyst supportive materials do not produce enough bioelectricity generation in the MFC.

In light of the above, a need remains for an eco-friendly, renewable system and a method of using the system for providing and determining bioelectricity generation of a carbon cloth modified with at least one of camel hair derived-polypeptide conjugated carbon quantum dots (CH-CQDs)-metal hybrid nanoarchitectures.

SUMMARY

The present subject matter relates to a method of making camel hair derived-polypeptide conjugated carbon quantum dots (CH-CQDs), as well as to a method of using the CH-CQDs to produce camel hair derived-polypeptide conjugated carbon quantum dots (CH-CQDs)-metal hybrid nanoarchitectures. The present subject matter further relates to a system and a method of using the system for providing and determining bioelectricity generation of a carbon cloth modified with at least one of the camel hair derived-polypeptide conjugated carbon quantum dots (CH-CQDs)-metal hybrid nanoarchitectures.

In one embodiment, the method of making camel hair derived-polypeptide conjugated carbon quantum dots (CH-CQDs) includes obtaining camel hair; mixing the camel hair with water to obtain a mixture; heating the mixture to obtain a heated mixture; cooling the heated mixture to obtain a cooled mixture; centrifuging the cooled mixture to obtain camel hair derived-polypeptide conjugated carbon quantum dots (CH-CQDs); and filtering the camel hair derived-polypeptide conjugated carbon quantum dots (CH-CQDs) from the cooled mixture.

In a further embodiment, the present subject matter relates to camel hair derived-polypeptide conjugated carbon quantum dots (CH-CQDs) prepared by the above method.

In a non-limiting embodiment, the mixture can be prepared by mixing about 5 g, or 5 g, of the camel hair with about 250 mL, or 250 ml. of deionized water. That is, according to this non-limiting embodiment, the mixture can be prepared by combining the camel hair with the deionized water in a ratio of 1:50, or about 1:50, w/v. For the avoidance of doubt, other weight: volume ratios are further contemplated as within the scope of the present subject matter.

In another embodiment, the heated mixture can be prepared by placing the mixture inside of a hydrothermal autoclave reactor and heating the mixture at about 200° C., or 200° C., for about 8 hours, or 8 hours.

In an additional non-limiting embodiment, the centrifuging the cooled mixture can be conducted at about 10000 rpm, or 10000 rpm for about 5 minutes, or 5 minutes. For the avoidance of doubt, other speeds and times for conducting the centrifuging of the cooled mixture are further contemplated as within the scope of the present subject matter. For example, this centrifuging step can be conducted at about 9000 rpm to about 11000 rpm, or 9000 rom to 11000 rpm, for about 3-7 minutes, or for 3-7 minutes.

In a further embodiment, the present subject matter relates to a method of making camel hair derived-polypeptide conjugated carbon quantum dots (CH-CQDs)-metal hybrid nanoarchitectures, wherein the method can include optionally preparing a plurality of mixtures of water and the above camel hair derived-polypeptide conjugated carbon quantum dots (CH-CQDs) to obtain a plurality of camel hair derived-polypeptide conjugated carbon quantum dots (CH-CQDs) solutions; preparing a plurality of metal precursor solutions; individually adding one of each of the plurality of metal precursor solutions to one of each of the plurality of camel hair derived-polypeptide conjugated carbon quantum dots (CH-CQDs) solutions to obtain a plurality of resultant mixtures; and individually mixing each of the plurality of resultant mixtures to obtain a plurality of camel hair derived-polypeptide conjugated carbon quantum dots (CH-CQDs)-metal hybrid nanoarchitectures.

In a further embodiment, the present subject matter relates to camel hair derived-polypeptide conjugated carbon quantum dots (CH-CQDs)-metal hybrid nanoarchitectures prepared by the above method.

In an embodiment, the plurality of camel hair derived-polypeptide conjugated carbon quantum dots (CH-CQDs) solutions can be used to prepare the camel hair derived-polypeptide conjugated carbon quantum dots/metal hybrid nanoarchitectures.

In another embodiment, each of the plurality of metal precursor solutions can be 0.001 M, or about 0.001M, metal precursor solutions in about 10 mL, or 10 mL, of water. In this regard, in an embodiment, each of the plurality of metal precursor solutions can be combined with one of the plurality of CH-CQDs solutions in a ratio of 2:1, or about 2:1, v/v.

In an additional embodiment, each of the plurality of metal precursor solutions can be one of palladium chloride, copper sulfate, silver nitrate, chloroplatinic acid, and chloroauric acid.

In a supplementary, non-limiting embodiment, each of the plurality of camel hair derived-polypeptide conjugated carbon quantum dots (CH-CQDs)-metal hybrid nanoarchitectures can be prepared by individually mixing each of the plurality of resultant mixtures at about 300 rpm, or 300 rpm, for about 6 hours, or 6 hours, for example, via a magnetic stirrer. For the avoidance of doubt, other speeds and times for mixing step are further contemplated as within the scope of the present subject matter. For example, this mixing step can be conducted at about 250 rpm to about 350 rpm, or 250 rom to 350 rpm, for about 5-7 hours, or for 5-7 hours.

In a further embodiment, each of the plurality of camel hair derived-polypeptide conjugated carbon quantum dots (CH-CQDs)-metal hybrid nanoarchitectures can be selected from one of the group consisting of camel hair derived-polypeptide conjugated carbon quantum dots-palladium nanoparticles (CH-CQDs/Pd), camel hair derived-polypeptide conjugated carbon quantum dots-copper nanoparticles (CH-CQDs/Cu), camel hair derived-polypeptide conjugated carbon quantum dots-silver nanoparticles (CH-CQDs/Ag), camel hair derived-polypeptide conjugated carbon quantum dots-platinum nanoparticles (CH-CQDs/Pt), and camel hair derived-polypeptide conjugated carbon quantum dots-gold nanoparticles (CH-CQDs/Au).

In an embodiment, the camel hair derived-polypeptide conjugated carbon quantum dots (CH-CQDs) can be stabilizing and reduction agents.

In another embodiment, the camel hair derived-polypeptide conjugated carbon quantum dots (CH-CQDs) can be yellow-colored.

In an additional embodiment, the mixing step can cause the color of the palladium chloride, the copper sulfate, the silver nitrate, the chloroplatinic acid, and the chloroauric acid in each of the plurality of resultant mixtures to turn amber, black, tan brown, brown, and olive, respectively.

In a further embodiment, the present subject matter relates to a system which includes a microbial fuel cell (MFC) in communication with a data acquisition system. The microbial fuel cell can include an anode comprising a carbon cloth and can be configured to contain wastewater and anaerobic sludge. The microbial fuel cell can also include a cathode connected to the anode via a conducting wire and can be configured to contain phosphate buffer saline. The cathode can include a carbon cloth modified with at least one of the camel hair derived-polypeptide conjugated carbon quantum dots (CH-CQDs)-metal hybrid nanoarchitectures, as discussed herein. In this regard, different camel hair derived-polypeptide conjugated carbon quantum dots (CH-CQDs)-metal hybrid nanoarchitectures are contemplated as within the scope of the present subject matter, including but not limited to CH-CQDs/Ag, CH-CQDs/Au, CH-CQDs/Pd, CH-CQDs/Cu, CH-CQDs/Pt, and the like. In an embodiment, one or more of the CH-CQDs/metal hybrids can be applied on the carbon cloth for electrode modification in a microbial fuel cell system. In another embodiment, one of the CH-CQDs/metal hybrids can be applied on the carbon cloth for electrode modification in a microbial fuel cell system. In a further embodiment, more than one of the CH-CQDs/metal hybrids can be applied on the carbon cloth for electrode modification in a microbial fuel cell system.

In certain embodiments, the microbial cell can further include a membrane located between the anode and the cathode. The data acquisition system can include a sensor connected to the conducting wire and can be configured to measure a voltage between the anode and the cathode. The data acquisition system can also include a data logger in communication with the sensor and can be configured to record the voltage. The data acquisition system can further include a computer with integrated software in communication with the data logger and can be configured to display the voltage measurement from the sensor.

In a further embodiment, the present subject matter relates to a method of using the above system for determining bioelectricity generation of the carbon cloth modified with at least one of the camel hair derived-polypeptide conjugated carbon quantum dots (CH-CQDs)-metal hybrid nanoarchitectures, wherein the method can include supplying the wastewater and/or the anaerobic sludge to the anode; supplying the phosphate buffer saline to the cathode; measuring the voltage between the anode and the cathode via the sensor; and determining the bioelectricity generation of the carbon cloth modified with at least one of the camel hair derived-polypeptide conjugated carbon quantum dots (CH-CQDs)-metal hybrid nanoarchitectures based on the measured voltage via the software.

In an embodiment, the least one of the camel hair derived-polypeptide conjugated carbon quantum dots (CH-CQDs)-metal hybrid nanoarchitectures can be selected from the group consisting of camel hair derived-polypeptide conjugated carbon quantum dots-palladium nanoparticles (CH-CQDs/Pd), camel hair derived-polypeptide conjugated carbon quantum dots-copper nanoparticles (CH-CQDs/Cu), camel hair derived-polypeptide conjugated carbon quantum dots-silver nanoparticles (CH-CQDs/Ag), camel hair derived-polypeptide conjugated carbon quantum dots-platinum nanoparticles (CH-CQDs/Pt), camel hair derived-polypeptide conjugated carbon quantum dots-gold nanoparticles (CH-CQDs/Au), and a combination thereof.

In another embodiment, the bioelectricity generation of the carbon cloth modified with the camel hair derived-polypeptide conjugated carbon quantum dots-palladium nanoparticles (CH-CQDs/Pd) can be 0.69 V.

In a further embodiment, the bioelectricity generation of the carbon cloth modified with the camel hair derived-polypeptide conjugated carbon quantum dots-platinum nanoparticles (CH-CQDs/Pt) can be 0.48 V. Accordingly, the bioelectricity generation of the carbon cloth modified with the camel hair derived-polypeptide conjugated carbon quantum dots-platinum nanoparticles (CH-CQDs/Pt) can be from 0.48 V to 0.69 V, or about 0.48 V to about 0.69 V.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
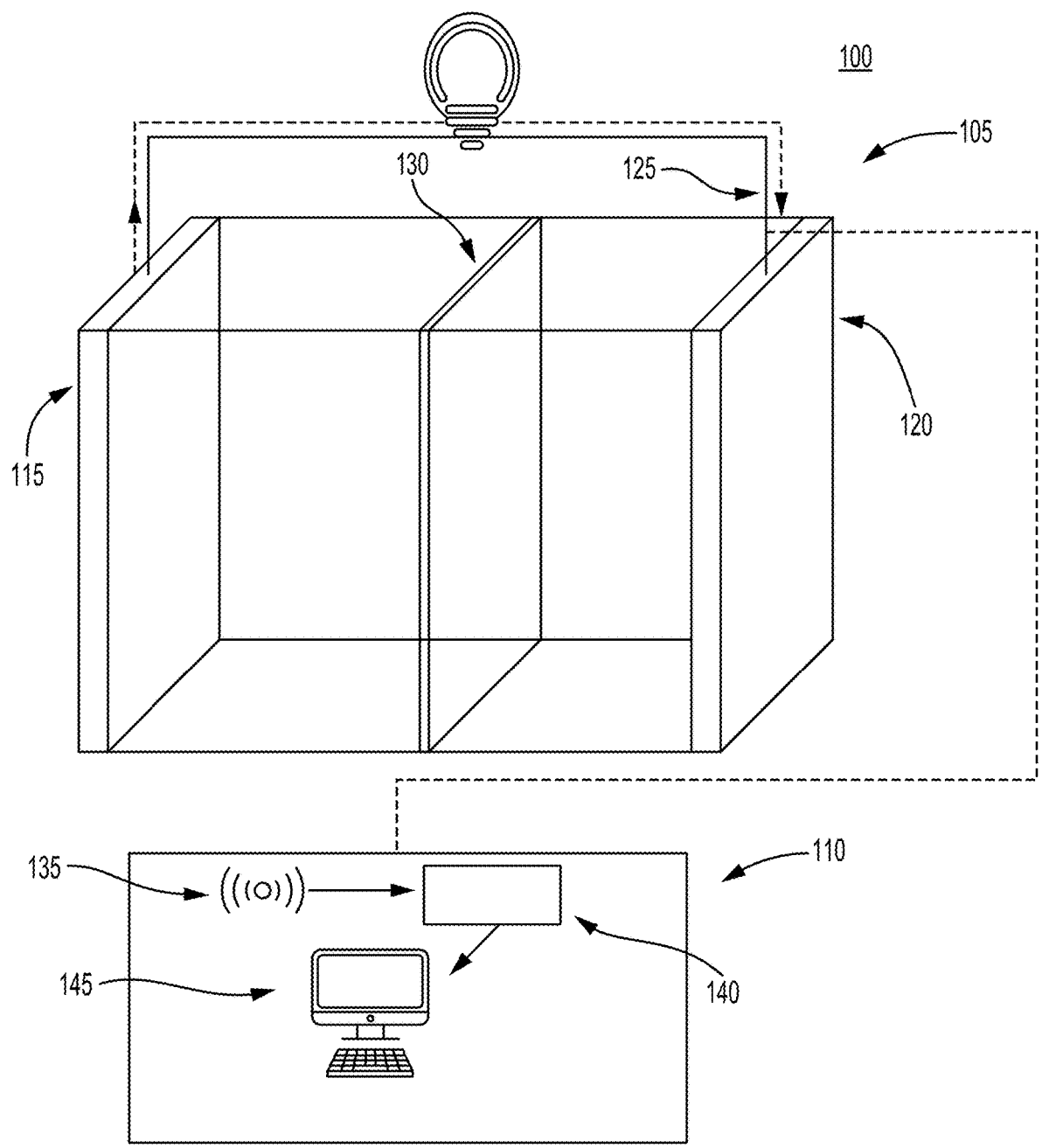
FIG. 1 depicts a system which includes a microbial fuel cell and a data acquisition system.

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method of making camel hair derived-polypeptide conjugated carbon quantum dots (CH-CQDs) and using the CH-CQDs to produce camel hair derived-polypeptide conjugated carbon quantum dots (CH-CQDs)-metal hybrid nanoarchitectures. The present subject matter further relates to a method of using a system for determining bioelectricity generation of the carbon cloth modified with at least one of the camel hair derived-polypeptide conjugated carbon quantum dots (CH-CQDs)-metal hybrid nanoarchitectures, as well as providing the bioelectricity generation therefrom.

In one embodiment, the method of making camel hair derived-polypeptide conjugated carbon quantum dots (CH-CQDs) includes obtaining camel hair; mixing the camel hair with water to obtain a mixture; heating the mixture to obtain a heated mixture; cooling the heated mixture to obtain a cooled mixture; centrifuging the cooled mixture to obtain camel hair derived-polypeptide conjugated carbon quantum dots (CH-CQDs); and filtering the camel hair derived-polypeptide conjugated carbon quantum dots (CH-CQDs) from the cooled mixture.

In a further embodiment, the present subject matter relates to camel hair derived-polypeptide conjugated carbon quantum dots (CH-CQDs) prepared by the above method.

In one embodiment, the method can include obtaining camel hair, which can be collected from healthy camels. The camel hair can be washed with water, which can remove impurities from the camel hair. In an embodiment, about 5 g of the washed camel hair can be mixed with about 250 mL of deionized water to obtain a mixture. Then, the mixture can be placed inside of a hydrothermal autoclave reactor and the mixture can be heated at about 200° C. for about 8 hours. Unexpectedly, it was discovered that during the heating step at 200° C. for 8 hours, the camel hair structure was disintegrated into protein hydrolysates. After the heating step, the color of the mixture can turn brown. The heated mixture can be cooled to obtain a cooled mixture.

In an embodiment, the cooled mixture can be centrifuged at about 1000 rpm for about 5 minutes to obtain a supernatant containing yellow-colored camel hair derived-polypeptide conjugated carbon quantum dots (CH-CQDs). Afterward, the yellow-colored camel hair derived-polypeptide conjugated carbon quantum dots (CH-CQDs) can be filtered from the cooled mixture via, by way of non-limiting example, a 0.22 µM filter.

In a further embodiment, the present subject matter relates to a method of making camel hair derived-polypeptide conjugated carbon quantum dots (CH-CQDs)-metal hybrid nanoarchitectures, the method includes preparing a plurality of camel hair derived-polypeptide conjugated carbon quantum dots (CH-CQDs) in liquid form; preparing a plurality of metal precursor solutions; individually adding one of each of the plurality of metal precursor solutions to one of each of the plurality of camel hair derived-polypeptide conjugated carbon quantum dots (CH-CQDs) in liquid form to obtain a plurality of resultant mixtures; and individually mixing each of the plurality of resultant mixtures to obtain a plurality of camel hair derived-polypeptide conjugated carbon quantum dots (CH-CQDs)-metal hybrid nanoarchitectures.

In an embodiment, the present subject matter relates to camel hair derived-polypeptide conjugated carbon quantum dots (CH-CQDs)-metal hybrid nanoarchitectures prepared by the above method.

In an embodiment, the method can include preparing a plurality of mixtures by adding the filtered CH-CQDs to about 5 mL of water to obtain a plurality of CH-CQDs solutions.

In an embodiment, a plurality of metal precursor solutions can be prepared by adding 0.001 M metal precursor solutions in about 10 mL of water. Each of the plurality of metal precursor solutions can include one of palladium chloride, copper sulfate, silver nitrate, chloroplatinic acid, and chloroauric acid.

In an embodiment, one of each of the plurality of metal precursor solutions can be individually added to one of each of the plurality of camel hair derived-polypeptide conjugated carbon quantum dots (CH-CQDs) solutions to obtain a plurality of resultant mixtures. Afterward, each of the plurality of resultant mixtures can be individually mixed at about 300 rpm for about 6 hours via a magnetic stirrer, causing the color of the palladium chloride, the copper sulfate, the silver nitrate, the chloroplatinic acid, and the chloroauric acid in each of the plurality of resultant mixtures to turn amber, black, tan brown, brown, and olive, respectively. As a result of the colors changing, a plurality of camel hair derived-polypeptide conjugated carbon quantum dots (CH-CQDs)-metal hybrid nanoarchitectures were obtained. In an embodiment, each of the plurality of camel hair derived-polypeptide conjugated carbon quantum dots (CH-CQDs)-metal hybrid nanoarchitectures can include one of the group consisting of camel hair derived-polypeptide conjugated carbon quantum dots-palladium nanoparticles (CH-CQDs/Pd) (derived from palladium chloride), camel hair derived-polypeptide conjugated carbon quantum dots-copper nanoparticles (CH-CQDs/Cu) (derived from copper sulfate), camel hair derived-polypeptide conjugated carbon quantum dots-silver nanoparticles (CH-CQDs/Ag) (derived from silver nitrate), camel hair derived-polypeptide conjugated carbon quantum dots-platinum nanoparticles (CH-CQDs/Pt) (derived from chloroplatinic acid), and camel hair derived-polypeptide conjugated carbon quantum dots-gold nanoparticles (CH-CQDs/Au) (derived from chloroauric acid).

Unexpectedly, it was discovered that during the mixing step at 300 rpm for 6 hours, the metal ions (i.e., $Pd^{2+}$, $Cu^{2+}$, $Ag^+$, $Pt^{2+}$, $Au^{3+}$) in the palladium chloride, the copper sulfate, the silver nitrate, the chloroplatinic acid, and the chloroauric acid, respectively, were reduced by the CH-CQDs and transformed into metal nanoparticles as described herein. The reason for this is because the CH-CQDs possess surface function groups (i.e., hydroxyl, carbonyl, and amine) that can trigger metal ion chelation and reduction. The metal ions were attached on the CH-CQDs anchoring sites during the adding step. Then, the metal ions were reduced into metal nanoparticles (indicated by the mentioned colors change) by the CH-CQDs during the mixing step at the mentioned speed and duration. Due to its role, the camel hair derived-polypeptide conjugated carbon quantum dots (CH-CQDs) can act as stabilizing and reduction agents.

In a further embodiment, the present subject matter relates to a system (100) which includes a microbial fuel cell (MFC) (105) in communication with a data acquisition system (110) as shown in FIG. 1. The microbial fuel cell (105), which can be a dual MFC and can be made of acrylic glass tube, can include an anode (115) comprising an unmodified carbon cloth (not shown) and can be configured to contain wastewater (not shown) and anaerobic sludge (not shown) as depicted in FIG. 1. The microbial fuel cell (105) can also include a cathode (120) connected to the anode (115) via a conducting wire (125) and can be configured to contain phosphate buffer saline (not shown) as shown in FIG. 1. In a non-limiting embodiment, the conducting wire (125) can be selected from the group consisting of titanium, stainless steel, graphene, carbon-based materials (i.e., graphite rods, carbon cloth, carbon paper, carbon felt, and reticulated vitreous carbon), and a combination thereof. The cathode (120) can include a carbon cloth modified with at least one of the camel hair derived-polypeptide conjugated carbon quantum dots (CH-CQDs)-metal hybrid nanoarchitectures (not shown).

In this regard, different camel hair derived-polypeptide conjugated carbon quantum dots (CH-CQDs)-metal hybrid nanoarchitectures are contemplated as within the scope of the present subject matter for use in obtaining the modified carbon cloth as described herein, including but not limited to CH-CQDs/Ag, CH-CQDs/Au, CH-CQDs/Pd, CH-CQDs/Cu, CH-CQDs/Pt, and the like. In an embodiment, one or more of the CH-CQDs/metal hybrids can be applied on the carbon cloth for electrode modification in a microbial fuel cell system. In another embodiment, one of the CH-CQDs/metal hybrids can be applied on the carbon cloth for electrode modification in a microbial fuel cell system. In a further embodiment, more than one of the CH-CQDs/metal hybrids can be applied on the carbon cloth for electrode modification in a microbial fuel cell system.

The microbial fuel cell (105), as depicted in FIG. 1, can further include a membrane (130), which in certain embodiments can be a proton exchange membrane for transferring cations from the anode (115) to the cathode (120), located between the anode (115) and the cathode (120). In another non-limiting embodiment, the membrane (130) can be selected from the group consisting of Nafion 117™ (Chemours company), polypropylene, polyvinylidene fluoride, sulfonated poly ether ether ketone, and a combination thereof.

The data acquisition system (110) can include a sensor (135) connected to the conducting wire (125) and can be configured to measure a voltage between the anode (115) and the cathode (120). In a further embodiment, the sensor (135) can be a multimeter or an Arduino UNO. The data acquisition system (110) can also include a data logger (140) in communication with the sensor (135) and can be configured to record the voltage. The data acquisition system (110) can further include a computer (145) with an integrated software in communication with the data logger (140) and can be configured to display the voltage measurement from the sensor (135).

In a further embodiment, the present subject matter relates to a method of using the above system (100) for determining bioelectricity generation of the carbon cloth modified with at least one of the camel hair derived-polypeptide conjugated carbon quantum dots (CH-CQDs)-metal hybrid nanoarchitectures, wherein the method includes supplying the wastewater and the anaerobic sludge to the anode (115); supplying the phosphate buffer saline to the cathode (120); measuring the voltage between the anode (115) and the cathode (120) via the sensor (135); and determining the bioelectricity generation of the carbon cloth modified with at least one of the camel hair derived-polypeptide conjugated carbon quantum dots (CH-CQDs)-metal hybrid nanoarchitectures based on the measured voltage via the software. In this regard, in an embodiment, the electricity measurement system can have built-in software capable of making such voltage measurements.

In an embodiment, the method can include supplying about 50 mL of the wastewater and about 1 mL of the anaerobic sludge to the anode (115). In an additional non-limiting embodiment, the wastewater can be dairy industrial effluent. The dairy industrial effluent can be selected from the group consisting of milk or milk products (i.e., spilled milk, spoiled milk, skimmed milk, cured milk, and starter cultures), processing by-products (i.e., whey and whey permeates), additives used for manufacturing milk, organic matters (i.e., lactose, fat, whey protein, fatty acid, and carbohydrate), nutrients (i.e., nitrogen and phosphorous), and a combination thereof. In certain non-limiting embodiments, the anaerobic sludge can be anaerobic bacteria and other microorganisms such as a microbial inoculant. In an embodiment, the cathode (120) can be supplied with phosphate buffer saline. After supplying the wastewater, the anaerobic sludge, and the phosphate buffer saline, the voltage between the anode (115) and the cathode (120) can be measured via the sensor (135). The measured voltage can be sent to the data logger (140) for recording the voltage. The recorded voltage can be sent to the computer (145) to display the voltage measurement from the sensor (135).

In this regard, the organic substances of dairy wastewater can be oxidized to produce electron and protons under anaerobic conditions. According to this embodiment, the electrons flow through the anode to the cathode, and the protons pass through a proton exchange membrane to the cathode.

In an embodiment, the software integrated within the computer (145) can also determine the bioelectricity generation of the carbon cloth modified with at least one of the camel hair derived-polypeptide conjugated carbon quantum dots (CH-CQDs)-metal hybrid nanoarchitectures based on the measured voltage. The at least one of the camel hair derived-polypeptide conjugated carbon quantum dots (CH-CQDs)-metal hybrid nanoarchitectures can be applied as an electrocatalyst. In an embodiment, the at least one of the camel hair derived-polypeptide conjugated carbon quantum dots (CH-CQDs)-metal hybrid nanoarchitectures can be selected from the group consisting of camel hair derived-polypeptide conjugated carbon quantum dots-palladium nanoparticles (CH-CQDs/Pd), camel hair derived-polypeptide conjugated carbon quantum dots-copper nanoparticles (CH-CQDs/Cu), camel hair derived-polypeptide conjugated carbon quantum dots-silver nanoparticles (CH-CQDs/Ag), camel hair derived-polypeptide conjugated carbon quantum dots-platinum nanoparticles (CH-CQDs/Pt), camel hair derived-polypeptide conjugated carbon quantum dots-gold nanoparticles (CH-CQDs/Au), and a combination thereof. In a further embodiment, the polypeptide conjugated CH-CQDs-metal hybrids can act as an electrocatalyst in the cathode reaction of microbial fuel cells. In this regard, the software can work like a multimeter to assist in the process.

Figure 2:
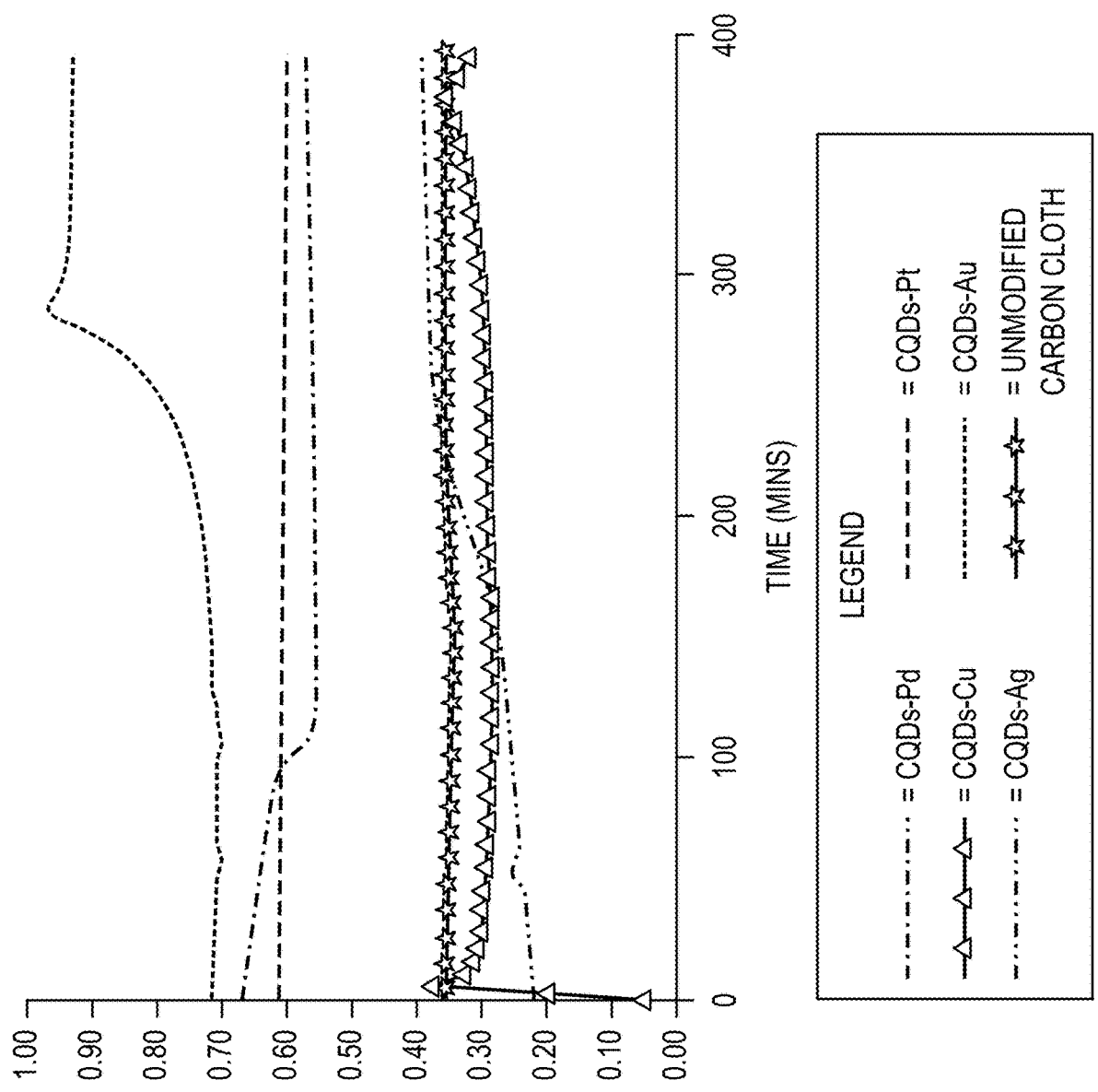
FIG. 2 depicts bioelectricity generation of a carbon cloth modified with at least one camel hair derived-polypeptide conjugated carbon quantum dots (CH-CQDs)-metal hybrid nanoarchitectures based on measured voltage during an initial process of the microbial fuel cell.

FIG. 2 depicts, in an embodiment, the bioelectricity generation of the carbon cloth modified with at least one of the camel hair derived-polypeptide conjugated carbon quantum dots (CH-CQDs)-metal hybrid nanoarchitectures based on the measured voltage during the initial process (i.e., from 0 minute to about 400 minutes (6.66 hours)) of the microbial fuel cell (105). During each experiment run, which pertains to FIGS. 2 and 3 as described herein, the carbon cloth in the cathode (120) was modified with one of the camel hair derived-polypeptide conjugated carbon quantum dots (CH-CQDs)-metal hybrid nanoarchitectures (i.e., CH-CQDs/Pd, CH-CQDs/Cu, CH-CQDs/Ag, CH-CQDs/Pt, CH-CQDs/Au). During the initial process as shown in FIG. 2, all the camel hair derived-polypeptide conjugated carbon quantum dots (CH-CQDs)-metal hybrid nanoarchitectures (i.e., CH-CQDs/Pd, CH-CQDs/Cu, CH-CQDs/Ag, CH-CQDs/Pt, and CH-CQDs/Au) exhibited higher bioelectricity output (voltage) compared to the unmodified carbon cloth. The CH-CQDs/Pd, CH-CQDs/Pt, and CH-CQDs/Au had higher bioelectricity output compared to the CH-CQDs/Cu and the CH-CQDs/Ag, with the CH-CQDs/Au having the highest voltage value.

Figure 3:
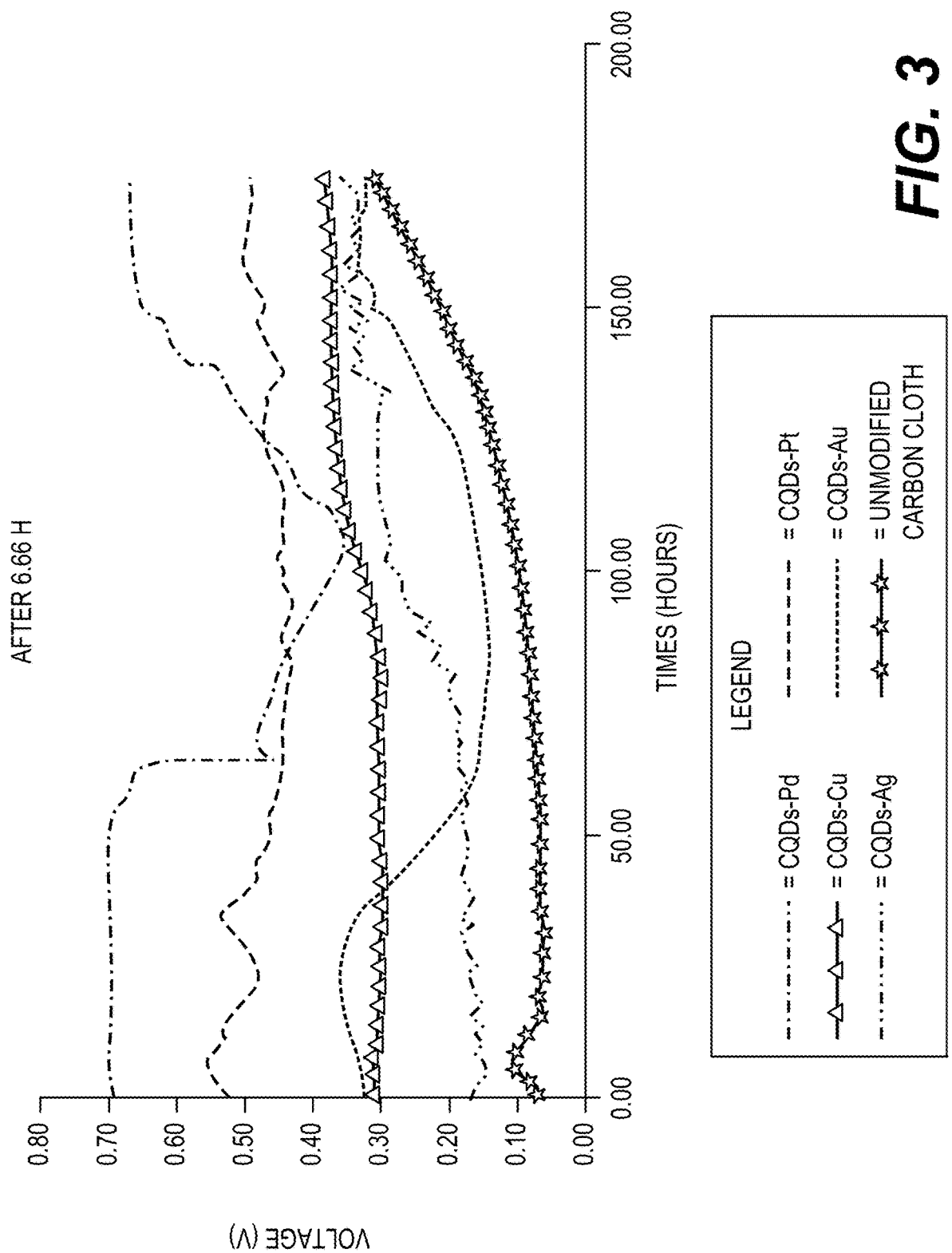
FIG. 3 depicts bioelectricity generation of a carbon cloth modified with at least one camel hair derived-polypeptide conjugated carbon quantum dots (CH-CQDs)-metal hybrid nanoarchitectures based on measured voltage after 6.66 hours during the operation of the microbial fuel cell.

However, after about 6.66 hours during the operation of the microbial fuel cell (105), the CH-CQDs/Pd exhibited the highest bioelectricity generation, at about 0.69 V as shown in FIG. 3. The CH-CQDs/Pt, CH-CQDs/Au, and CH-CQDs/Cu exhibited bioelectricity generation at about 0.48 V, about 0.36 V, and about 0.3 V, respectively. The CH-CQDs/Ag and the unmodified carbon cloth exhibited poor bioelectricity generation, at about 0.17 V and about 0.11 V, respectively. Based on these results, the performance of microbial fuel cells can be improved by the incorporation of the CH-CQDs/Pd, CH-CQDs/Pt, CH-CQDs/Au, and CH-CQDs/Cu, which boosts electrocatalysis within the microbial fuel cells. Accordingly, the microbial fuel cells as described herein, in certain embodiments, can exhibit bioelectricity generation of 0.3 V to 0.69 V, 0.48 to 0.69 V, or a range of any two voltage points, or about any two voltage points, as discussed herein.

While the camel hair derived-polypeptide conjugated carbon quantum dots (CH-CQDs)-metal hybrid nanoarchitectures have been used for the microbial fuel cell (105), other applications are possible. For example, the CH-CQDs/Ag and CH-CQDs/Cu can be used as antimicrobial agents. For cancer treatment, the CH-CQDs/Au and CH-CQDs/Pd can be used.

The following examples illustrate the present teachings.

EXAMPLES

Example 1

Synthesis of Polypeptide Conjugated Carbon Quantum Dots (CH-CQDs)

The process of synthesizing polypeptide conjugated carbon quantum dots was conducted using the following steps.

Collection of camel hair: Camel hair was collected from healthy camels from a local camel farm in Riyadh, Kingdom of Saudi Arabia. The camel hair was washed with water to remove impurities from the camel hair.

Mixing: About 5 g of the washed camel hair was mixed with about 250 mL of deionized water to obtain a mixture.

Hydrothermal autoclave reactor: The mixture was placed inside of a hydrothermal autoclave reactor and the mixture was heated at about 200° C. for about 8 hours. After the heating step, the color of the mixture turned brown.

Cooling: The heated mixture was cooled to obtain a cooled mixture.

Centrifuging: The cooled mixture was centrifuged at about 1000 rpm for about 5 minutes to obtain a supernatant containing yellow-colored camel hair derived-polypeptide conjugated carbon quantum dots (CH-CQDs).

Filtering: The yellow-colored camel hair derived-polypeptide conjugated carbon quantum dots (CH-CQDs) were filtered from the cooled mixture via 0.22 μM filter.

Example 2

Synthesis of Polypeptide Conjugated Carbon Quantum Dots (CH-CQDs)-Metal Hybrid Nanoarchitectures The process of synthesizing polypeptide conjugated carbon quantum dots-metal hybrid nanoarchitectures was conducted using the following steps.

Preparing a plurality of mixtures: Each of a plurality of mixtures was prepared by adding the filtered CH-CQDs to about 5 mL of water to obtain a plurality of CH-CQDs solutions.

Preparing a plurality of metal precursor solutions: Each of a plurality of metal precursor solutions was prepared by adding 0.001 M metal precursor solutions in about 10 mL of water. Each of the plurality of metal precursor solutions included one of palladium chloride, copper sulfate, silver nitrate, chloroplatinic acid, and chloroauric acid.

Preparing a plurality of resultant mixtures: One of each of the plurality of metal precursor solutions was individually added to one of each of the plurality of camel hair derived-polypeptide conjugated carbon quantum dots (CH-CQDs) solutions to obtain a plurality of resultant mixtures.

Mixing: Each of the plurality of resultant mixtures was individually mixed at about 300 rpm for about 6 hours via a magnetic stirrer, causing the color of the palladium chloride, the copper sulfate, the silver nitrate, the chloroplatinic acid, and the chloroauric acid in each of the plurality of resultant mixtures to turn amber, black, tan brown, brown, and olive, respectively. As a result of the colors changing, a plurality of camel hair derived-polypeptide conjugated carbon quantum dots (CH-CQDs)-metal hybrid nanoarchitectures were obtained. Each of the plurality of camel hair derived-polypeptide conjugated carbon quantum dots (CH-CQDs)-metal hybrid nanoarchitectures included one of the group consisting of camel hair derived-polypeptide conjugated carbon quantum dots-palladium nanoparticles (CH-CQDs/Pd) (derived from palladium chloride), camel hair derived-polypeptide conjugated carbon quantum dots-copper nanoparticles (CH-CQDs/Cu) (derived from copper sulfate), camel hair derived-polypeptide conjugated carbon quantum dots-silver nanoparticles (CH-CQDs/Ag) (derived from silver nitrate), camel hair derived-polypeptide conjugated carbon quantum dots-platinum nanoparticles (CH-CQDs/Pt) (derived from chloroplatinic acid), and camel hair derived-polypeptide conjugated carbon quantum dots-gold nanoparticles (CH-CQDs/Au) (derived from chloroauric acid).

Example 3

Transmission Electron Microscopy

Structural and morphological features of the polypeptide conjugated CH-CQDs-metal hybrid nanoarchitectures were investigated using a transmission electron microscopy (TEM) from JEOL (Tokyo, Japan) with an accelerating voltage of about 100 kV. The TEM images revealed palladium nanoparticles with sizes ranging from about 15 nm to about 25 nm, surrounded by well-dispersed spherical polypeptide conjugated CH-CQDs with sizes ranging from about 2 nm to about 10 nm. The TEM images also revealed copper nanoparticles with sizes ranging from about 35 nm to about 60 nm, surrounded by well-dispersed spherical polypeptide conjugated CH-CQDs with sizes ranging from about 1 nm to about 10 nm. As for the silver nanoparticles, the TEM images revealed nanoparticles sizes ranging from about 50 nm to about 125 nm, surrounded by well-dispersed spherical polypeptide conjugated CH-CQDs with sizes ranging from about 2 nm to about 20 nm. The TEM images also revealed platinum nanoparticles with sizes ranging from about 15 nm to about 25 nm, surrounded by well-dispersed spherical polypeptide conjugated CH-CQDs with sizes ranging from about 2 nm to about 10 nm. With respect to the gold nanoparticles, the TEM images revealed nanoparticles sizes ranging from about 50 nm to about 90 nm, or from 50 nm to 90 nm, surrounded by well-dispersed spherical polypeptide conjugated CH-CQDs with sizes ranging from about 5 nm to about 15 nm, or from 5 nm to 15 nm.

Example 4

Dynamic Light Scattering Technique

Figure 4:
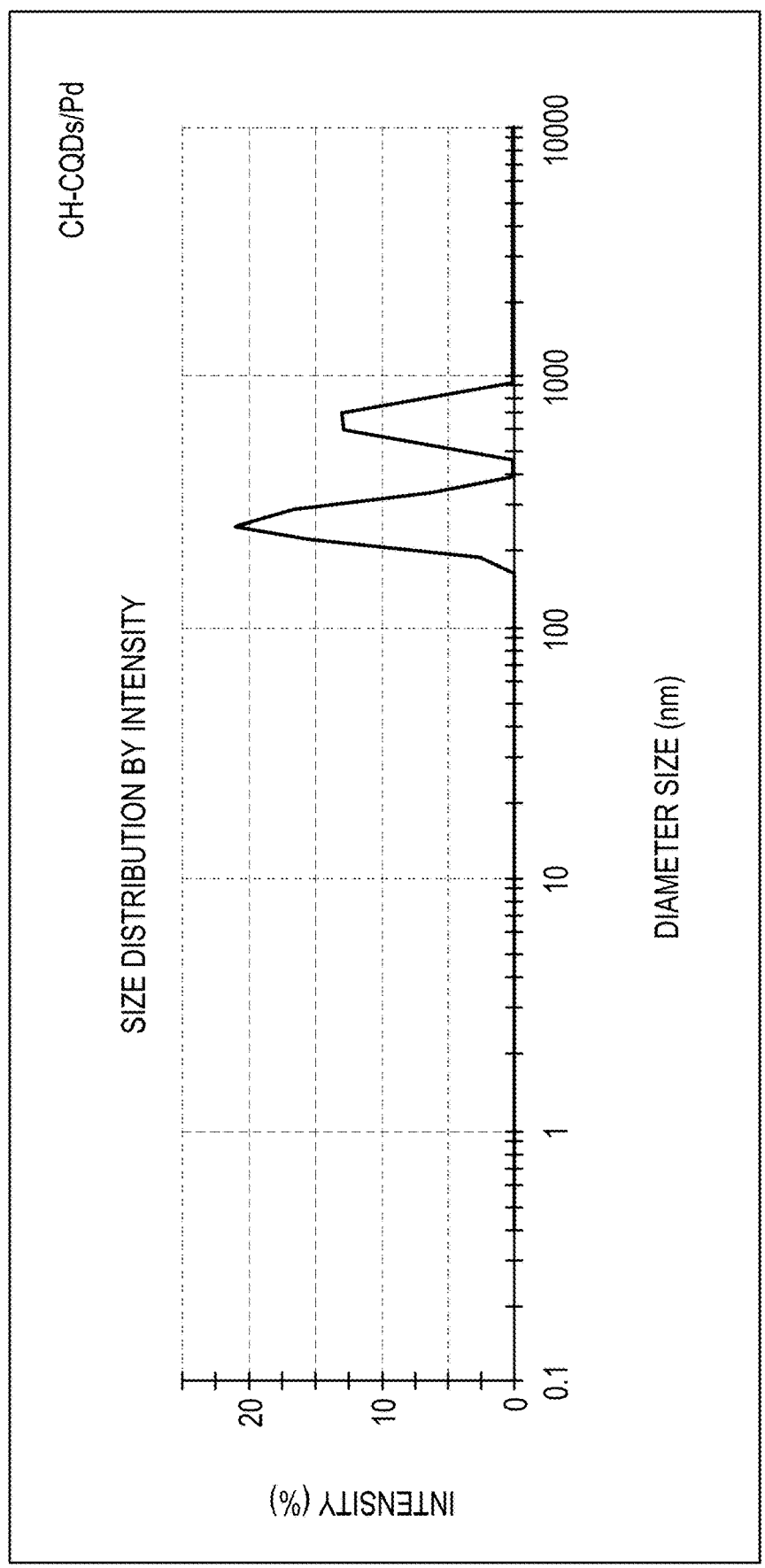
FIG. 4 depicts average particle diameter sizes of CH-CQDs/Pd.
Figure 5:
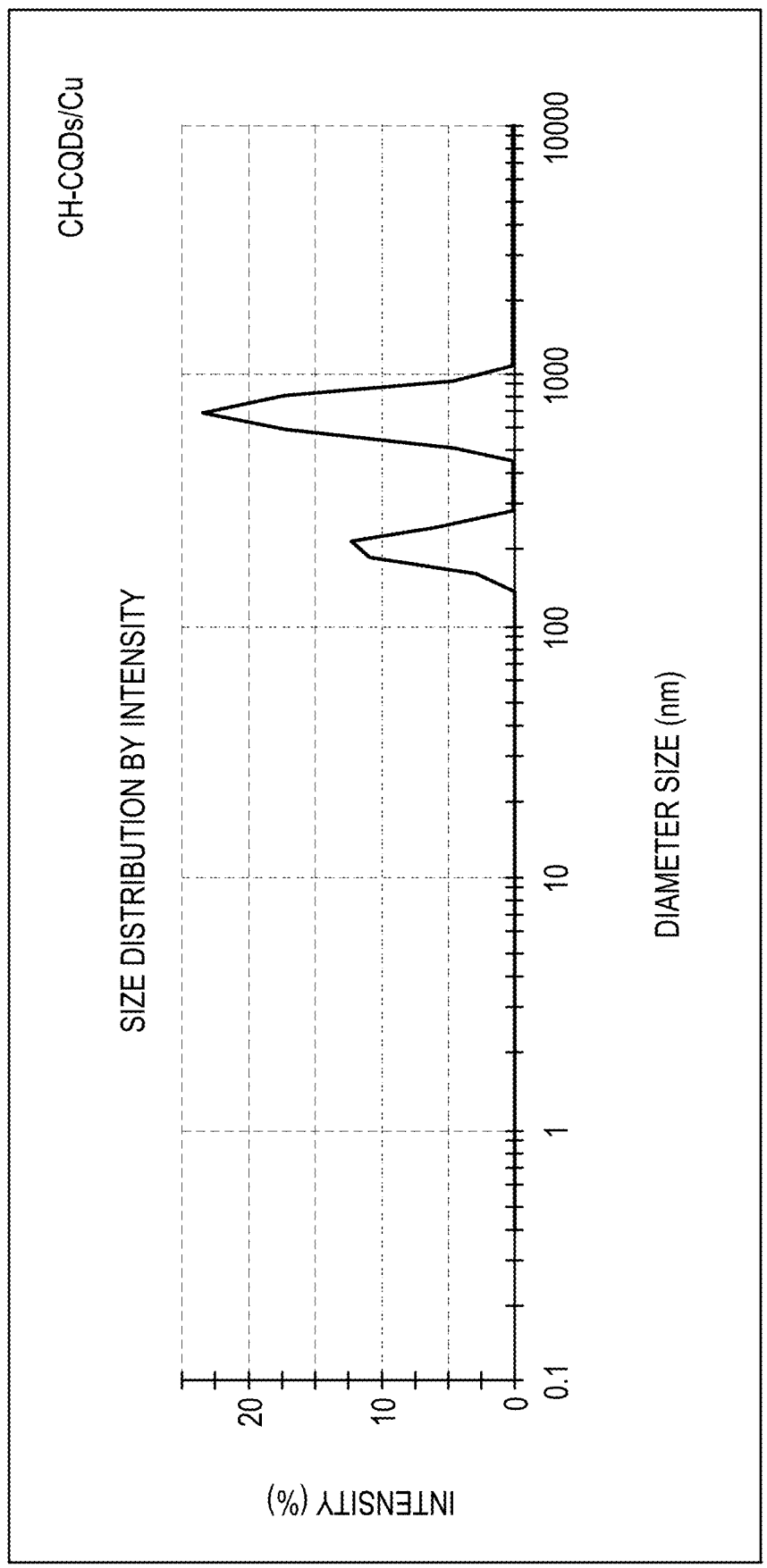
FIG. 5 depicts average particle diameter sizes of CH-CQDs/Cu.
Figure 6:
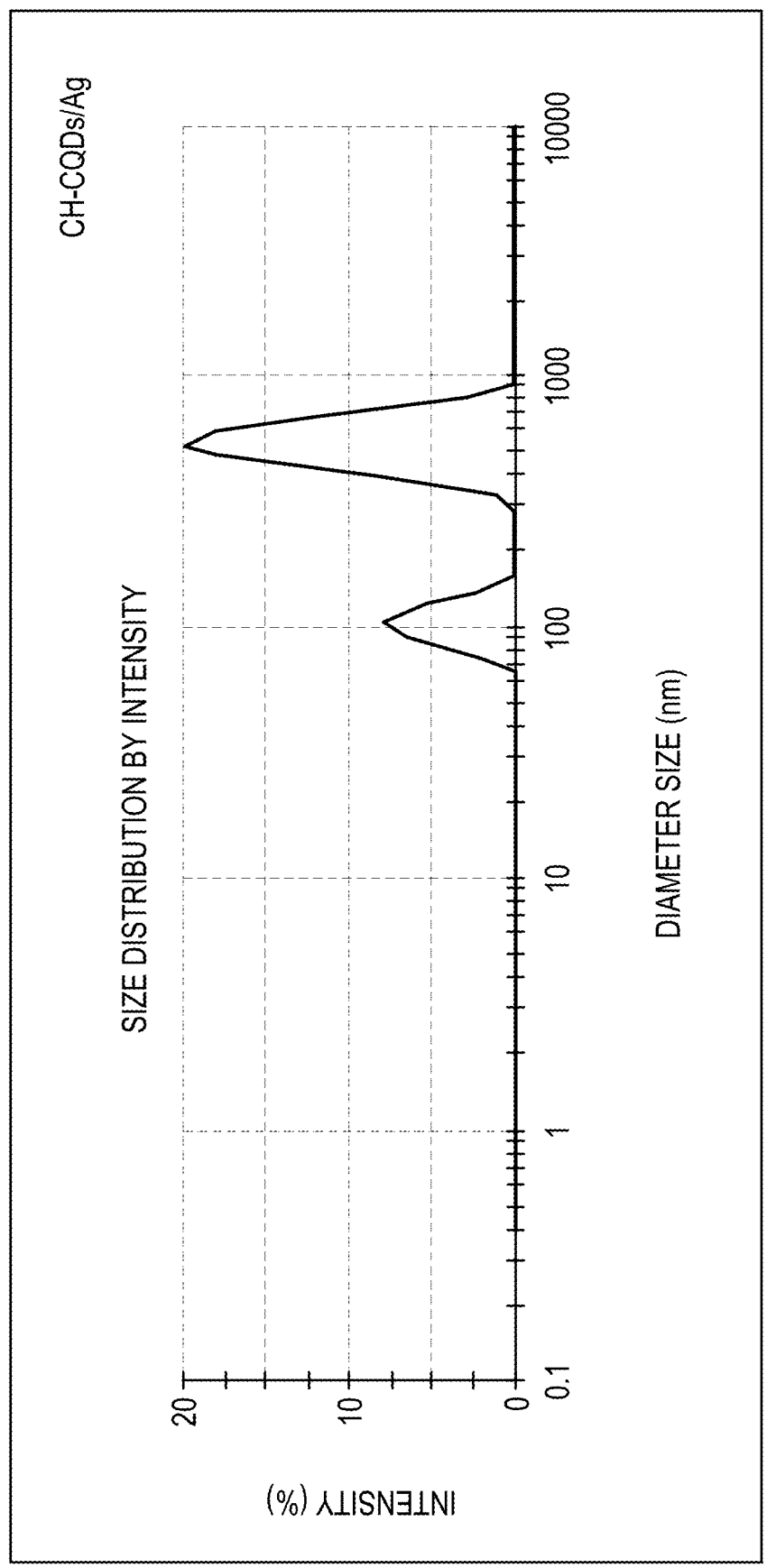
FIG. 6 depicts average particle diameter size of CH-CQDs/Ag.
Figure 7:
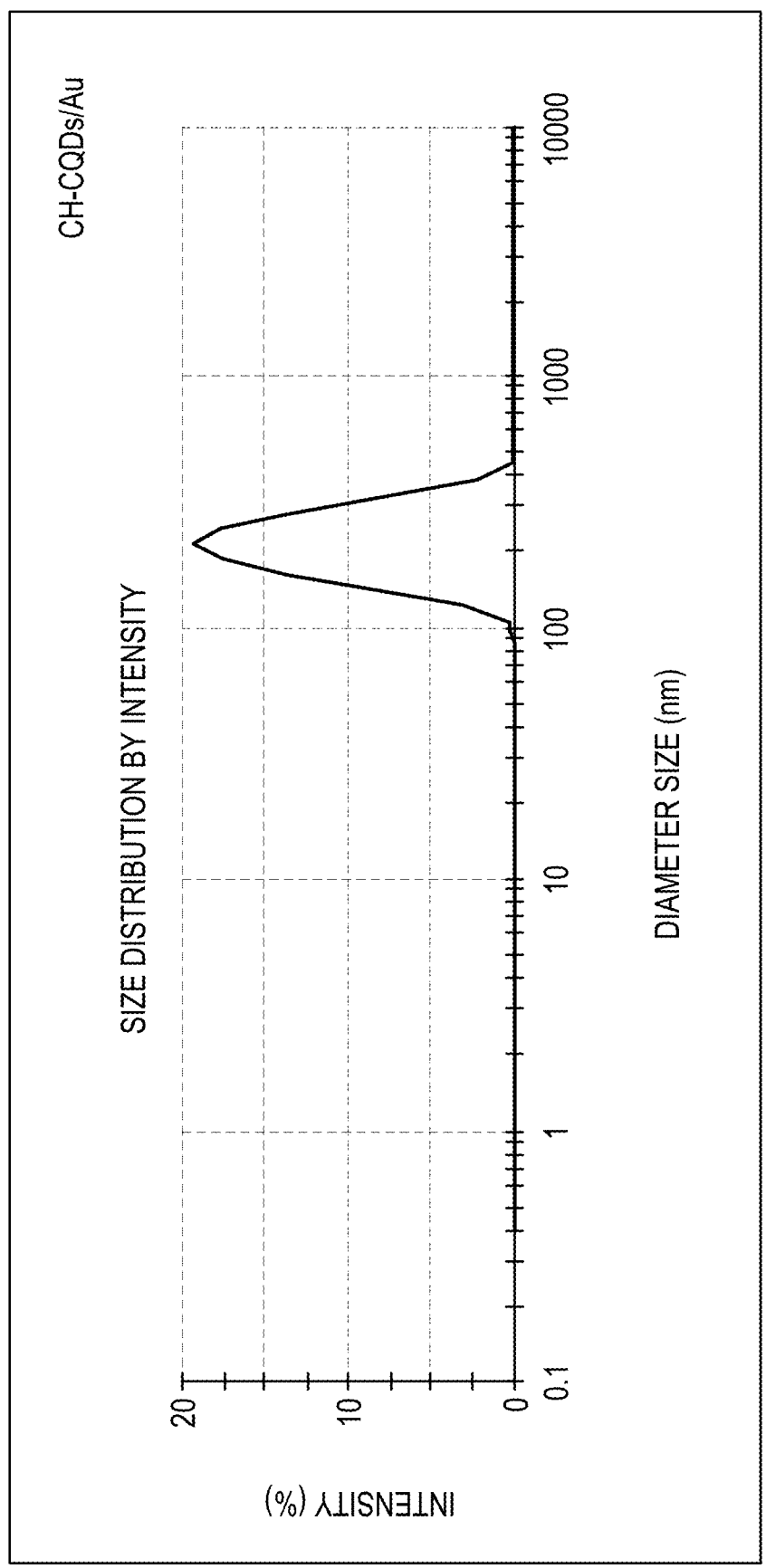
FIG. 7 depicts average particle diameter sizes of CH-CQDs/Au.

Average particle sizes of the CH-CQDs-metal hybrid nanoarchitectures were investigated using a Malvern Zetasizer 90S for dynamic light scattering. As depicted in FIG. 4, the CH-CQDs/Pd contains large and small average particle sizes. The CH-CQDs/Cu contains large and small average particle sizes, as shown in FIG. 5. As for the CH-CQDs/Ag, FIG. 6 depicts large and small average particle sizes. As shown in FIG. 7, the CH-CQDs/Au contains average particle size of about 236 nm.

Example 5

Ultraviolet-Visible Spectroscopy

Figure 8:
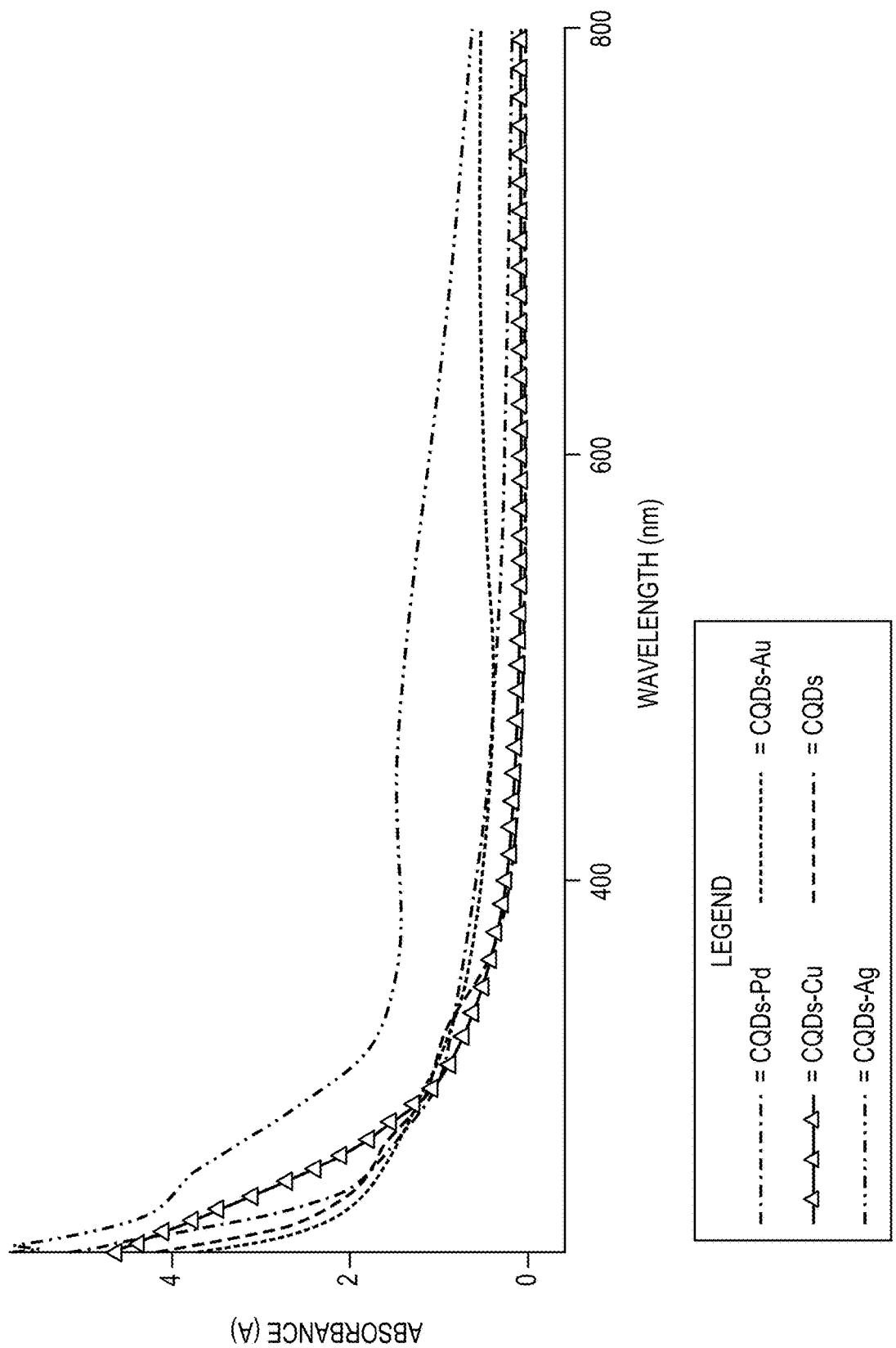
FIG. 8 depicts surface plasmon resonance broad band peaks of CQDs-Pd, CQDs-Cu, CQDs-Ag, CQDs-Au, and CQDs.

Optical behavior of the CH-CQDs-metal hybrid nanoarchitectures was investigated using an ultraviolet-visible spectroscopy. As depicted in FIG. 8, the CQDs-Pd, CQDs-Cu, CQDs-Ag, and CQDs-Au exhibited surface plasmon resonance broad band peaks at about 279 nm, about 267 nm, about 440 nm, and about 500 nm to about 800 nm, respectively, corresponding to the palladium nanoparticles, the copper nanoparticles, the silver nanoparticles, and the gold nanoparticles, respectively. The CQDs exhibited surface plasmon resonance broad band peak at about 281 nm.

Example 6

X-Ray Diffraction (XRD)

Crystal structures of the CH-CQDs-metal hybrid nanoarchitectures were investigated using an x-ray diffractometer as shown in FIGS. 9-12. The x-ray diffractometer was a Bruker D8 Advance with Cu Kα radiation and 100 mA current and 40 kV.

Figure 9:
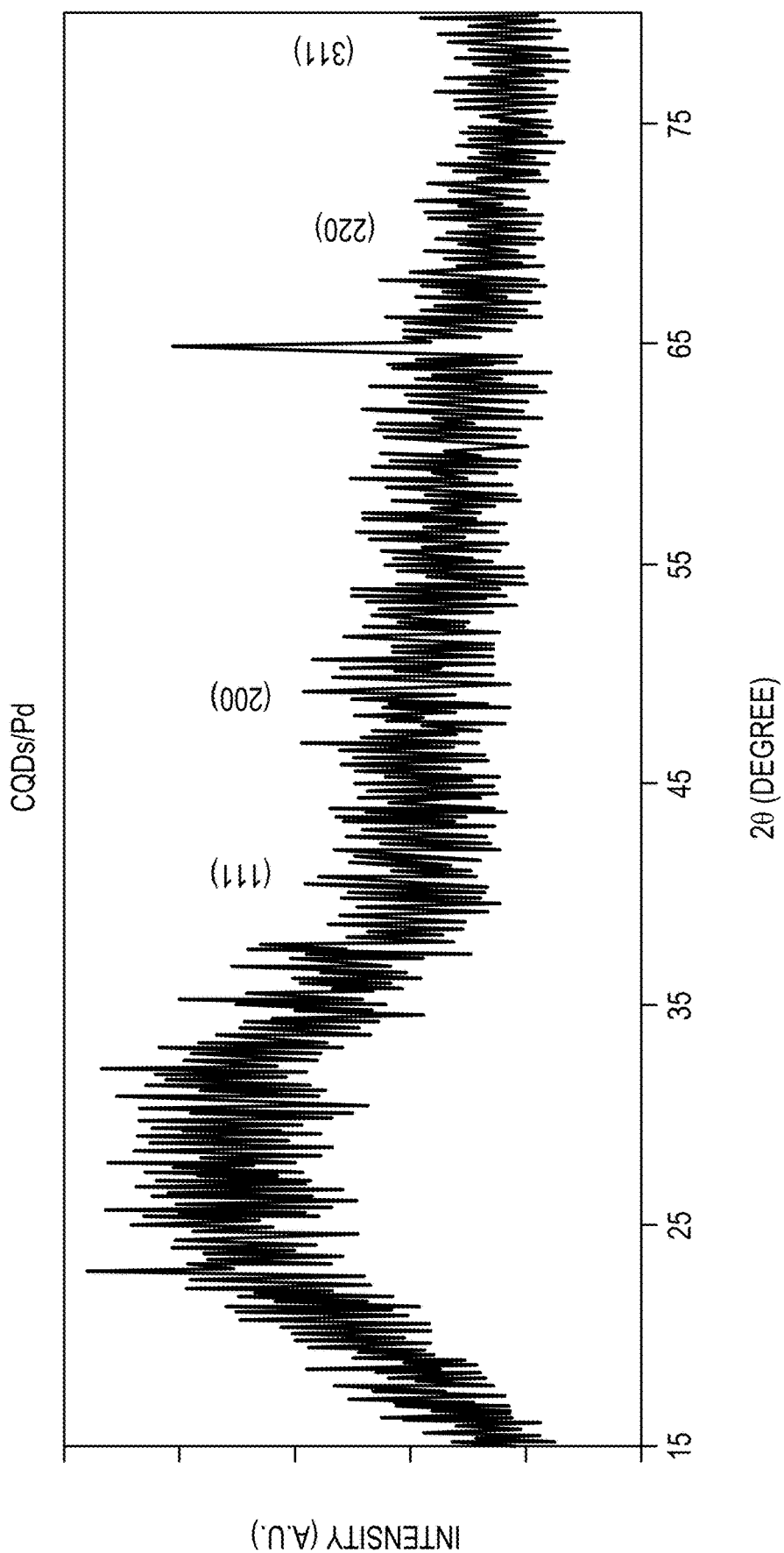
FIG. 9 depicts diffraction peaks of CH-CQDs/Pd.
Figure 10:
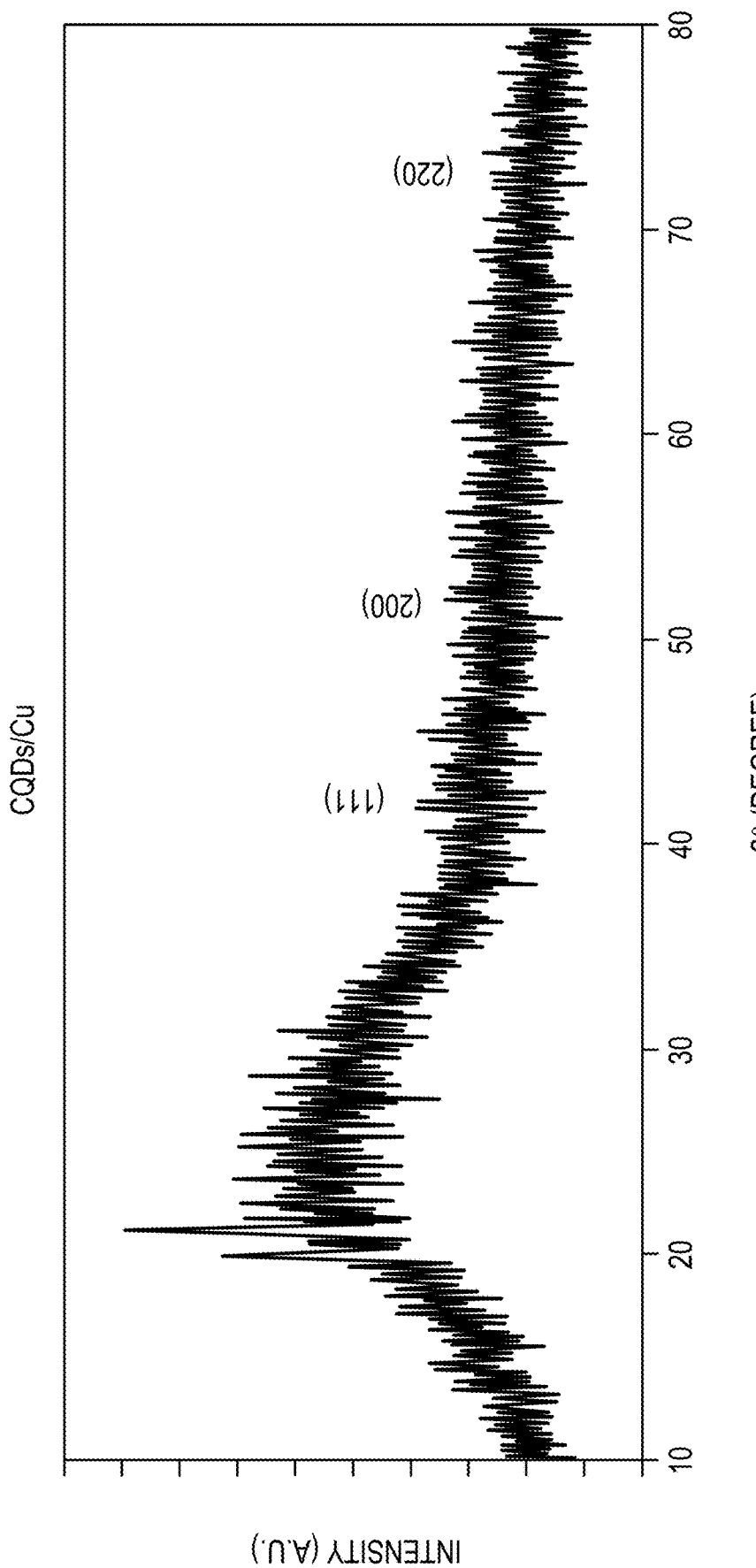
FIG. 10 depicts diffraction peaks of CH-CQDs/Cu.
Figure 11:
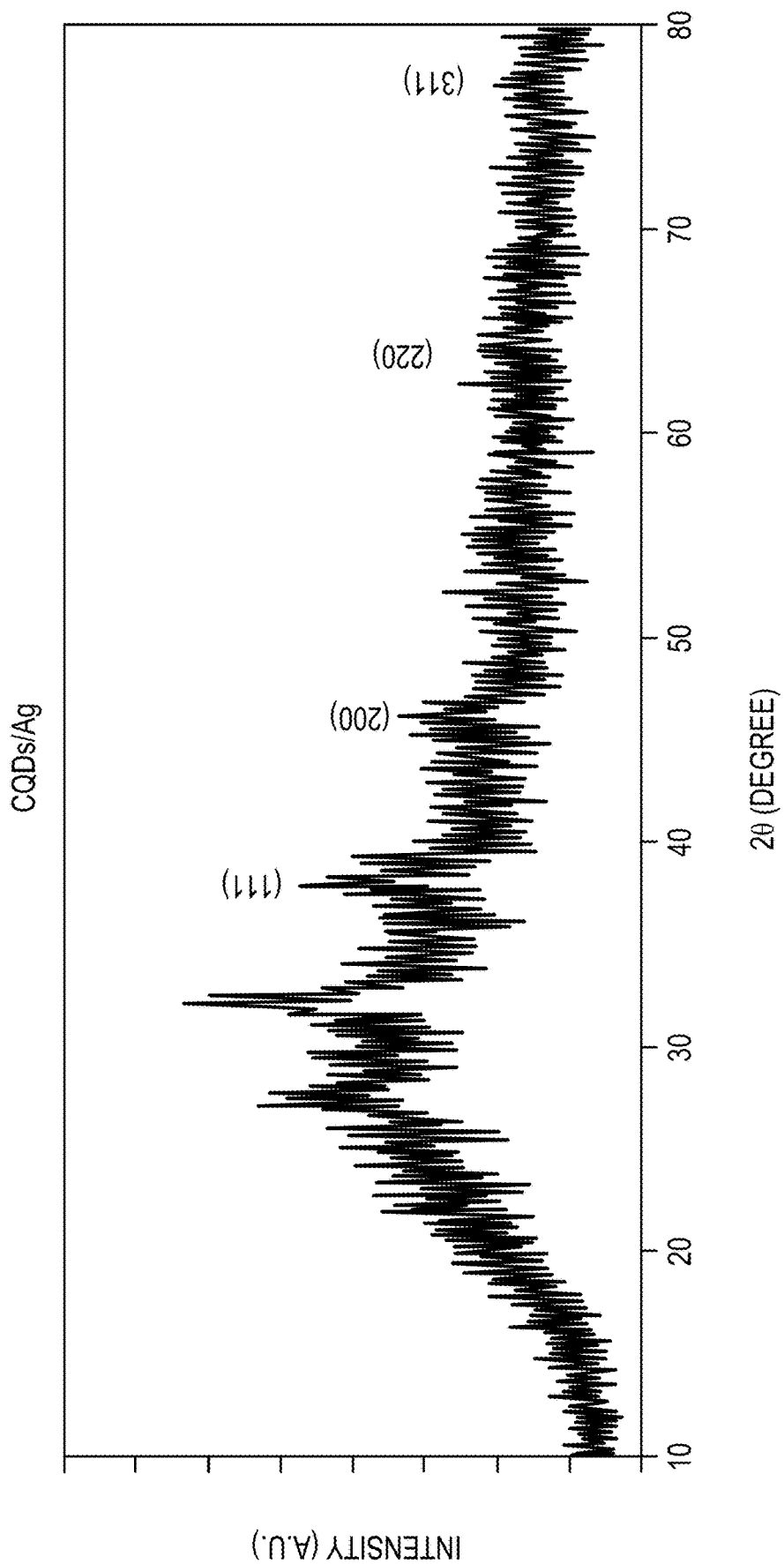
FIG. 11 depicts diffraction peaks of CH-CQDs/Ag.
Figure 12:
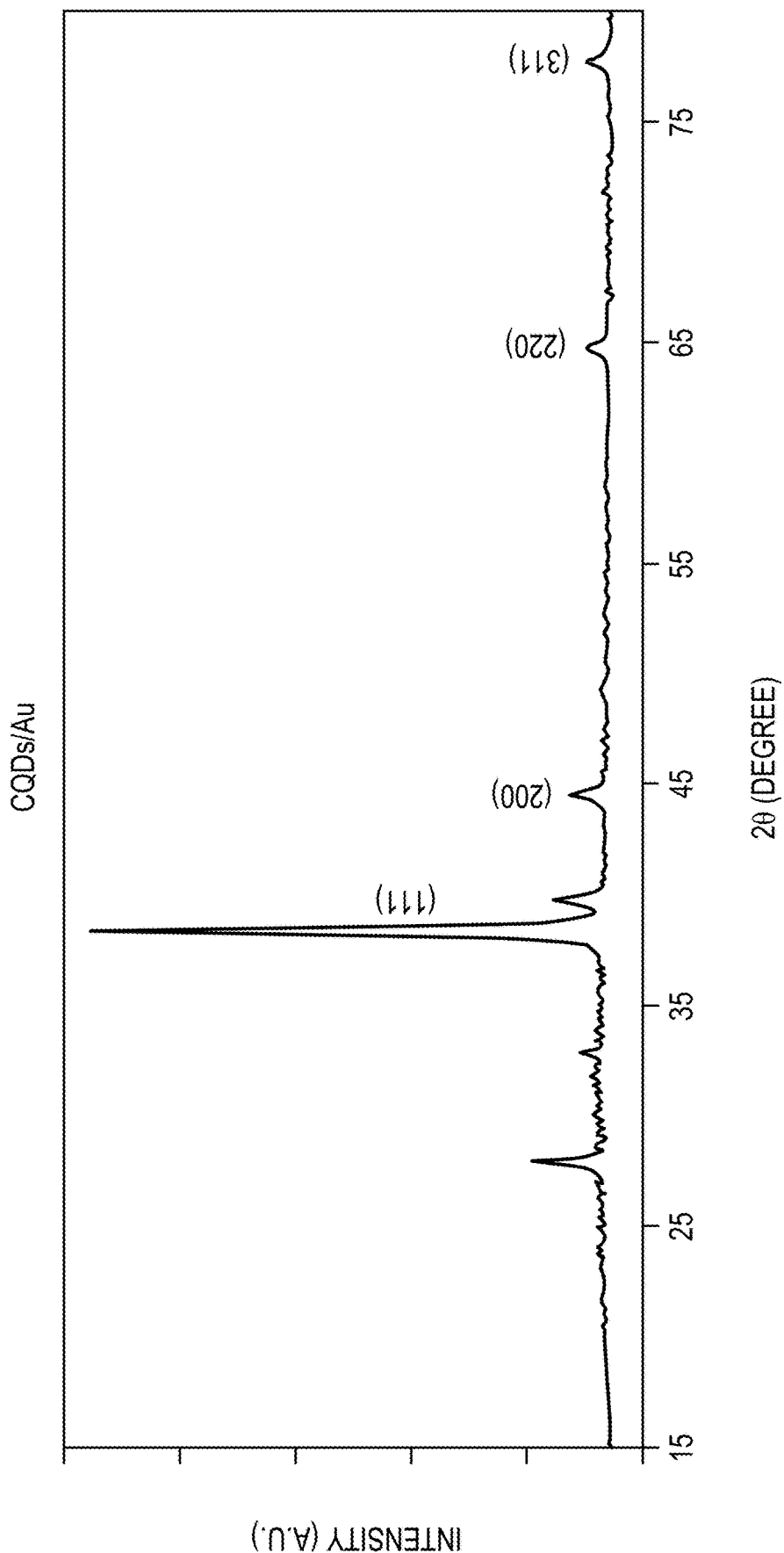
FIG. 12 depicts diffraction peaks of CH-CQDs/Au.

As depicted in FIG. 9, diffraction peaks of the CH-CQDs/Pd hybrid nanoarchitecture occurred at the 2θ values of about 40.2°, about 46.9°, about 68.3°, about 82.2°, representing the existence of about (111) lattice plane, about (200) lattice plane, about (220) lattice plane, and about (311) lattice plane of face-centered cubic structure of the palladium nanoparticles, respectively, on the CH-CQDs surface. In FIG. 10, the diffraction peaks of the CH-CQDs/Cu hybrid nanoarchitecture occurred at the 2θ values of about 43.2°, about 50.2° and about 74.3°, representing the existence of about (111) lattice plane, about (200) lattice plane, and about (220) lattice plane of face-centered cubic structure of the copper nanoparticles, respectively, on the CH-CQDs surface. FIG. 11 shows the diffraction peaks of the CH-CQDs/Ag hybrid nanoarchitecture occurred at 2θ values of about 38.1°, about 43.3°, about 64.2°, and about 77.2°, representing the existence of about (111) lattice plane, about (200) lattice plane, about (220) lattice plane, and about (311) lattice plane of face-centered cubic structure of the silver nanoparticles, respectively, on the CH-CQDs surface. The diffraction peaks of the CH-CQDs/Au hybrid nanoarchitecture, as depicted in FIG. 12, occurred at 2θ values of about 38.1°, about 43.5°, about 64.0°, and about 77.1°, representing the existence of about (111) lattice plane, about (200) lattice plane, about (220) lattice plane, and about (311) lattice plane of face-centered cubic structure of the gold nanoparticles, respectively, on the CH-CQDs surface. In this regard, for each of FIGS. 9-12, intensity is measured according to the Arbitrary Scale.

It is to be understood that the system, the method of making camel hair derived-polypeptide conjugated carbon quantum dots (CH-CQDs), the method of making camel hair derived-polypeptide conjugated carbon quantum dots (CH-CQDs)-metal hybrid nanoarchitectures, and the method of using the system for determining bioelectricity generation of the carbon cloth modified with at least one of the camel hair derived-polypeptide conjugated carbon quantum dots (CH-CQDs)-metal hybrid nanoarchitectures are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making camel hair derived-polypeptide conjugated carbon quantum dots (CH-CQDs)-metal hybrid nanoarchitectures, the method comprising:
    making the camel hair derived-polypeptide conjugated carbon quantum dots (CH-CQDs) by
        obtaining camel hair,
        mixing the camel hair with water to obtain a mixture,
        heating the mixture to obtain a heated mixture,
        cooling the heated mixture to obtain a cooled mixture,
        centrifuging the cooled mixture to obtain camel hair derived-polypeptide conjugated carbon quantum dots (CH-CQDs), and
        filtering the camel hair derived-polypeptide conjugated carbon quantum dots (CH-CQDs) from the cooled mixture;
    preparing the camel hair derived-polypeptide conjugated carbon quantum dots (CH-CQDs) in liquid form to obtain a plurality of camel hair derived-polypeptide conjugated carbon quantum dots (CH-CQDs) solutions;
    preparing a plurality of metal precursor solutions;
    individually adding one of each of the plurality of metal precursor solutions to one of each of the plurality of camel hair derived-polypeptide conjugated carbon quantum dots (CH-CQDs) solutions to obtain a plurality of resultant mixtures; and
    individually mixing each of the plurality of resultant mixtures to obtain a plurality of camel hair derived-polypeptide conjugated carbon quantum dots (CH-CQDs)-metal hybrid nanoarchitectures.

2. The method of claim 1, wherein the plurality of camel hair derived-polypeptide conjugated carbon quantum dots (CH-CQDs) in liquid form are prepared by adding the camel hair derived-polypeptide conjugated carbon quantum dots to about 5 mL of water.

3. The method of claim 1, wherein each of the plurality of metal precursor solutions are 0.001 M metal precursor solutions in about 10 mL of water.

4. The method of claim 3, wherein each of the plurality of metal precursor solutions comprise one of palladium chloride, copper sulfate, silver nitrate, chloroplatinic acid, and chloroauric acid.

5. The method of claim 1, wherein each of the plurality of camel hair derived-polypeptide conjugated carbon quantum dots (CH-CQDs)-metal hybrid nanoarchitectures were prepared by individually mixing each of the plurality of resultant mixtures at about 300 rpm for about 6 hours via a magnetic stirrer.

6. The method of claim 4, wherein each of the plurality of camel hair derived-polypeptide conjugated carbon quantum dots (CH-CQDs)-metal hybrid nanoarchitectures are selected from one of the group consisting of camel hair derived-polypeptide conjugated carbon quantum dots-palladium nanoparticles (CH-CQDs/Pd), camel hair derived-polypeptide conjugated carbon quantum dots-copper nanoparticles (CH-CQDs/Cu), camel hair derived-polypeptide conjugated carbon quantum dots-silver nanoparticles (CH-CQDs/Ag), camel hair derived-polypeptide conjugated carbon quantum dots-platinum nanoparticles (CH-CQDs/Pt), and camel hair derived-polypeptide conjugated carbon quantum dots-gold nanoparticles (CH-CQDs/Au).

7. The method of claim 1, wherein the camel hair derived-polypeptide conjugated carbon quantum dots (CH-CQDs) are stabilizing and reduction agents.

8. The method of claim 4, wherein the camel hair derived-polypeptide conjugated carbon quantum dots (CH-CQDs) are yellow-colored.

9. The method of claim 8, wherein the mixing step causes the color of the palladium chloride, the copper sulfate, the silver nitrate, the chloroplatinic acid, and the chloroauric acid in each of the plurality of resultant mixtures to turn amber, black, tan brown, brown, and olive, respectively.

10. The method of claim 8, wherein the palladium chloride, the copper sulfate, the silver nitrate, the chloroplatinic acid, and the chloroauric acid in each of the plurality of resultant mixtures to turn 15-25 nm palladium nanoparticles, 35-60 nm copper nanostructures, 50-125 nm silver nanoparticles, 15-25 nm platinum nanoparticles and 50-90 nm gold nanoparticles on polypeptide conjugated carbon quantum dots matrix, respectively.

11. Camel hair derived-polypeptide conjugated carbon quantum dots (CH-CQDs)-metal hybrid nanoarchitectures prepared by the method of claim 1.

* * * * *